United States Patent [19]

Schleich

[11] 4,128,942
[45] Dec. 12, 1978

[54] DENTAL ARTICULATOR

[75] Inventor: Hans B. Schleich, Nendeln, Liechtenstein

[73] Assignee: Etablissement Dentaire Ivoclar, Schaan, Liechtenstein

[21] Appl. No.: 746,576

[22] Filed: Dec. 1, 1976

[30] Foreign Application Priority Data

Dec. 3, 1975 [DE] Fed. Rep. of Germany ....... 2554410

[51] Int. Cl.² .............................................. A61C 11/00
[52] U.S. Cl. ................................................................. 32/32
[58] Field of Search ............................................. 32/32

[56] References Cited

U.S. PATENT DOCUMENTS

| 2,534,023 | 12/1950 | Hirchhorn | 32/32 |
| 2,550,043 | 4/1951 | De Lautour | 32/32 |
| 2,613,440 | 10/1952 | Murray et al. | 32/32 |

FOREIGN PATENT DOCUMENTS 134489 10/1949 Australia ........................................ 32/32

*Primary Examiner*—Louis G. Mancene
*Assistant Examiner*—G. Lee Skillington
*Attorney, Agent, or Firm*—Sprung, Felfe, Horn, Lynch & Kramer

[57] ABSTRACT

An improvement in a dental articulator having a pair of opposed mountings each of which is itself mounted on arms adjustable and fixable in relationship to the opposed mounting and each of which has a spherical axial bearing for adjustably connecting a support for one of the mandibular and maxillary models the dental articulator being improved in that each of said spherical axial bearings is mounted at a sliding bushing, said sliding bushing axially adjustably and fixably disposed in a bore, said bore provided within each of said arms.

12 Claims, 3 Drawing Figures

DENTAL ARTICULATOR

BACKGROUND OF THE INVENTION

1. Field of The Invention

The invention relates to an articulator having two mountings mounted on its arms and adjustable and fixable in relation to one another, the said mountings having holders or supports, one for the mandibular model and the other for the maxillary model, and being disposed on adjustable, spherical axial bearings.

Such an articulator, which, among other things, reproduces the movement of the mandibular articulation, makes it possible to fix the two corresponding plaster casts of the patient's jaws in the attitude in which they would meet in their natural position in the patient's mouth. The correctly positioned transfer is accomplished by known means, such as face bows, a wax index, horizontal guides etc. With the fastening of the plaster model, which can be accomplished in a single procedure for both casts, or separately for the maxilla and mandible, the mechanically set simulation of the natural jaw movement is possible, which is essential to the further operations.

2. Discussion of The Prior Art

The fastening of the plaster jaw models in the articulator is accomplished by the use of plaster, whereby the plaster cast is joined to its mechanical holder as used in the apparatus. The mechanical holders or supports can consist, for example, of a holding yoke, which is molded into the model. These model holding yokes can also be attached to the articulator by a stud connector. It is furthermore known (U.S. Pat. No. 2,621,407) to fasten the model to the arms of the articulator by means of ball joints, the ball joint for the maxillary model being locked in relation to the articulation of the articulator, thereby simultaneously preventing any change in the level of the plane of occlusion with respect to the articulation. The cross table movements to the performed in the horizontal plane can be achieved only with the mandibular model or model holder, two sliding members being provided which are adjustable at right angles and disposed one above the other, and which are fixable by means of screws in each case.

Merely to coordinate the mandibular model with the maxillary model, numerous screws must therefore be adjusted or set independently of one another, which renders continuous shifting of the mandibular model unfeasible, the danger additionally existing that previously set adjustments might be altered.

Other known articulators have claws for gripping the plaster model. These models can easily be removed, but they cannot be installed with reference to coordinates, and they do not permit arbitrary alignment or three-dimensional adjustment of the two models to one another. Furthermore, it is not possible to perform corrections of the positions of the plaster casts as might appear necessary or desirable, by means of the holding device.

It is therefore the object of the present invention to expand the usefulness of such an articulator and to achieve a coordinate-referenced alignment of the two jaw models with one another and with the mandibular articulation and articulator articulation without having to alter the fastening of the model to its mounting for this purpose.

SUMMARY OF THE INVENTION

In accordance with the foregoing this invention broadly contemplates a dental articulator which achieves coordinate-referenced alignment of a pair of opposed jaw models with respect to one another and with the mandibular articulation and articulator articulation without requiring the refastening of the model for such purposes. Hence, the present invention contemplates an improvement in a dental articulator having a pair of opposed mountings each of which is itself mounted on arms adjustable and fixable in relationship to the opposed mountings each of which has supports disposed on an adjustable spherical axial bearing for a mandibular or maxillary model which dental articulator is improved in that each of such spherical axial bearings is at least partially contained within an axially adjustable and fixable sliding bushing, said sliding bushing adjustably disposed in a bore, said bore disposed within said arm.

The objects of this invention are provided because the spherical axial bearing is associated with an axially adjustable and lockable sliding sleeve or bushing which in turn is guided within a bore in the arms of the dental articulator. In the following description reference will be made to the position of the sliding bushing in the arm of the dental articulator. In a preferred embodiment of the invention the arm has two limbs. Thus the term "arm" is also intended to cover the term "limbs" where applicable, it being understood that the sliding bush or sleeve is disposed in a limb-like or arm-like member which is usually opposed to a second limb-like or arm-like member provided for the purpose of mounting thereto an opposed mounting member on which a model will be placed.

In this manner, a high-quality, individually adjustable articulator imitating all human jaw movements is created, which is quick to set up, and which operates with the highest precision. Even after long usage, its precision is not impaired by the unavoidable incrustation, since it is not necessary to send the articulator into the plaster casting room for the purpose of fastening the plaster model obtained from the dentist's impression in the desired position in the articulator by means of plaster or cements. By the attachment of the model to the articulator in accordance with the invention, one can put the plaster model into any desired position without the use of fresh plaster. Both the mandibular model and the maxillary model can be placed and locked in any necessary position in relation to one another and to the mandibular articulation on the basis of the axial displaceability of the mountings, of the spherical bearings, and of the substantially horizontal adjustability of the model holder in relation to the mountings. Desirably, the mountings with the holders or plaster models are removable from the articulator and can be returned to the original position with any desired frequency. Thus, with this articulator, work models of different patients can be installed and removed continually, as needed. The insertion and removal do not require that the plaster model be removed from the holder, but instead the entire mounting can be removed from the articulator and reinstalled, without danger of damage to the plaster model.

BRIEF DESCRIPTION OF DRAWINGS

Referring to the accompanying drawings showing a preferred embodiment of the invention.

DESCRIPTION OF SPECIFIC EMBODIMENTS

Figure 1:
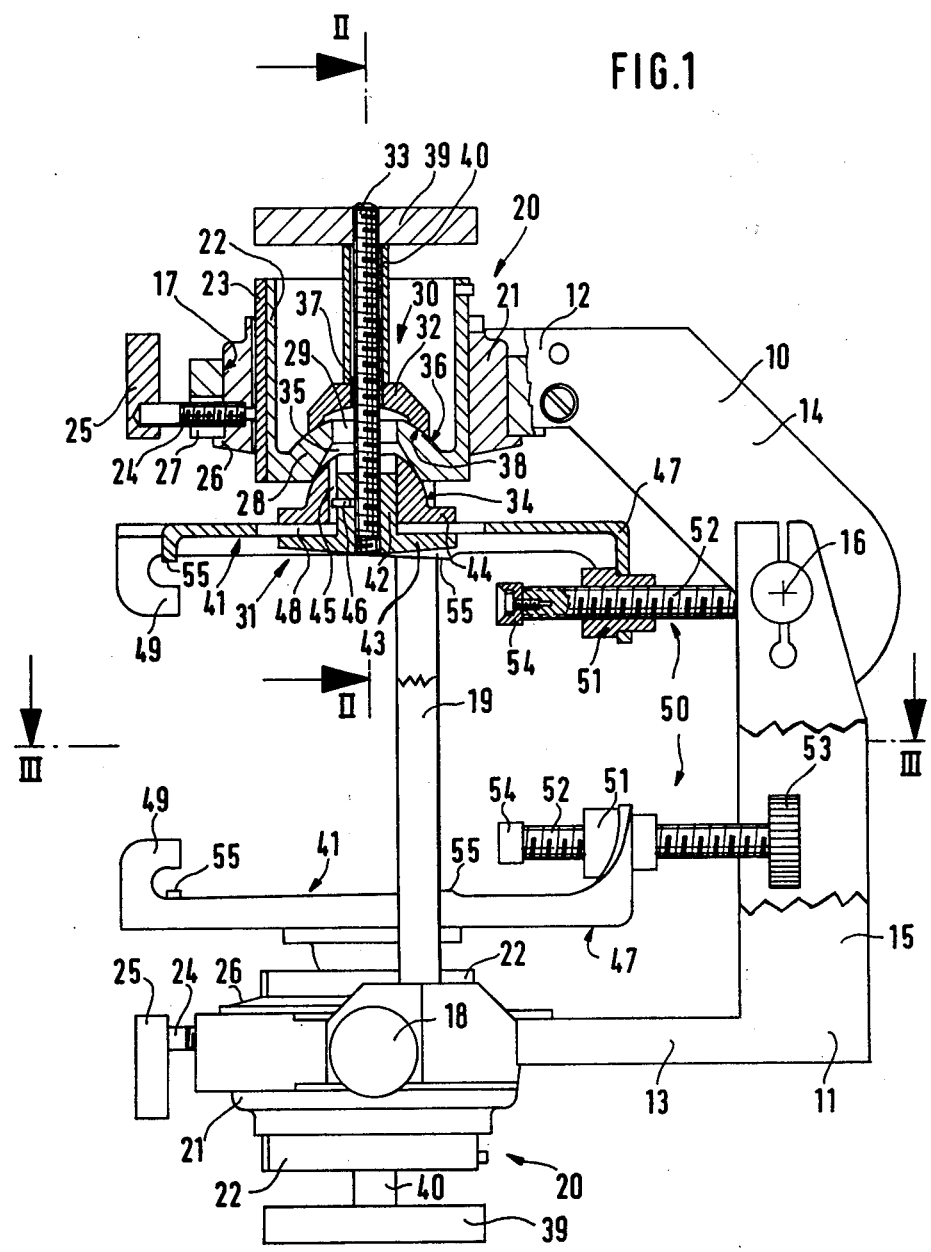
FIG. 1 is a side elevational view, partially in cross section, of the articulator.
Figure 2:
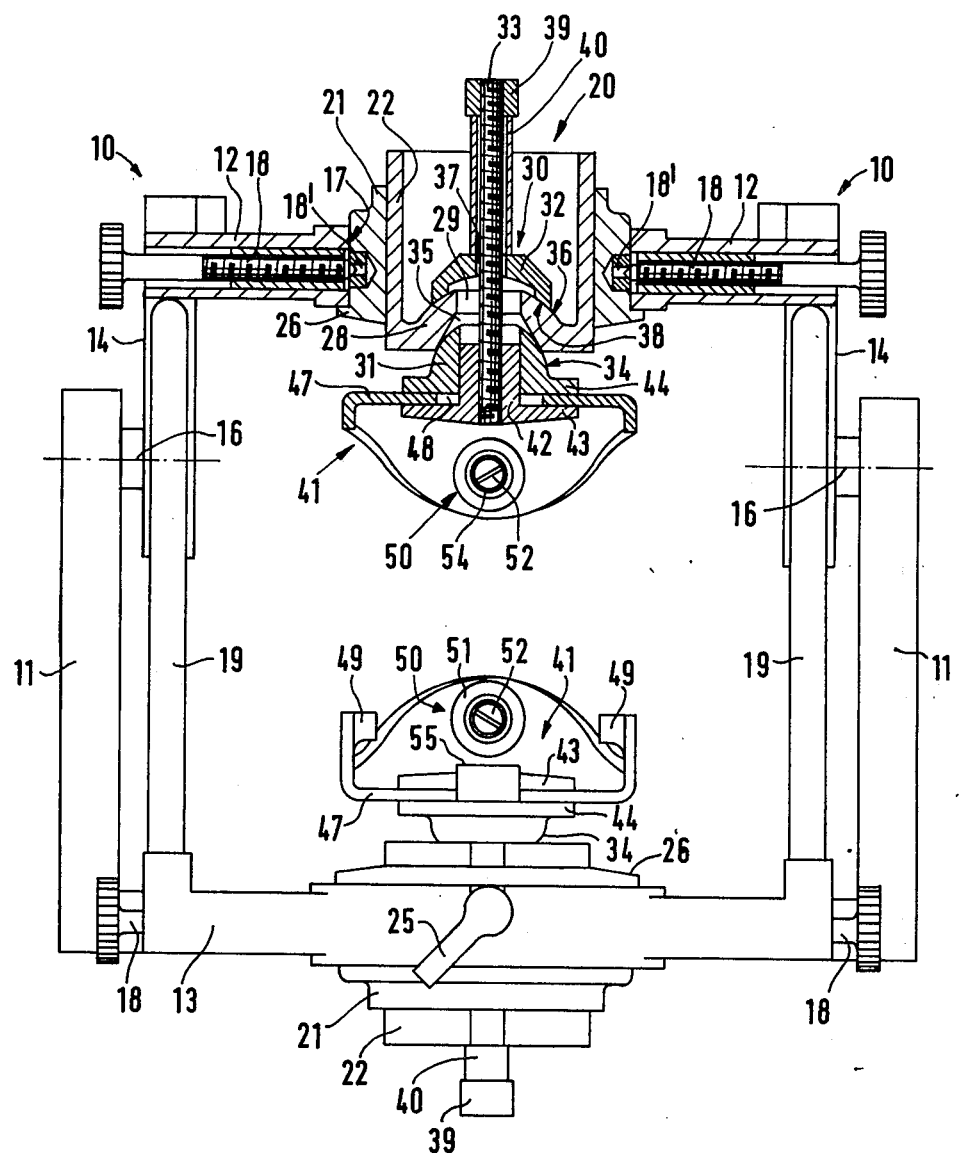
FIG. 2 is a front elevational view, partially in a cross section taken along line II—II in FIG. 1.

The articulator consists essentially of two bent arms 10 and 11 which are formed of the free limbs 12 and 13 as well as limbs 14 and 15, which are joined to one another pivotingly about an axis 16. In this manner the arms 10 and 11 can be brought into various positions. FIG. 1 shows the neutral operating position in which the free limbs 12 and 13 are substantially parallel to one another.

Each of the free limbs 12 and 13, which are preferably constructed as a plate, is provided with an aperture 17 in which mountings 20 for the mandibular and maxillary models, which are not shown, can be fixed by means of two diametrically opposed screws 18. Between the free limbs 12 and 13, spacing pins 19 serve, after the rotation of the arms 10 and 11, to support the models once again in the neutral working position. The models can be removed from the articulator 10–17 together with the model mountings 20. The articulator can then be used for another patient's models fastened on other mountings 20.

The mountings 20 consist of a bearing ring 21 which has centering bores 18' for the centering screws 18, and in which a sleeve 22 is mounted for axial displacement such that the sleeves 22 in the opposite free limbs 12 and 13 can be moved toward and away from one another.

The bearing ring 21 and the sleeve 22 each have a groove, the two grooves being located in a confronting relationship and accommodating a key 23 which, by means of screw 24 threaded through the bearing ring 21, can be urged inwardly against the sleeve 22 such that sleeve 22 can be locked axially in relation to the bearing ring 21. For this purpose the screw 24 is provided with an externally accessible handle 25.

Conveniently, the aperture 17 in the limbs 12 and 13 is in the form of a bore into which the model mounting 20 is inserted, the bearing ring 21 having a flange 26 which aligns the bearing ring 21 axially within the bore 17. In this embodiment, a groove 27 that is open in the direction of the flange 26 is associated with bore 17 for the screw 24 with the handle 25.

The sleeve 22 has an inner wall 28 having a central bore 29. The wall 28 forms a fixed bearing for a spherical axial bearing 30. On both sides of the fixed bearing 28 there are provided bearing elements 31 and 32 which are joined together by means of a bolt 33 which extends through the bore 29. The main element 31 has a spherical bearing surface 34 which is placed in a concave recess 35 in the wall or fixed bearing 28. The concave recess 35 is of truncoconical shape in the embodiment represented, although it can also have a surface of a configuration to match the spherical bearing surface 34.

On the side facing the counterplate 32, the wall or fixed bearing 28 likewise has a spherical bearing surface 36 which cooperates with the counterplate 32 in the form of a ring. The bolt 33 extends through a central bore 37 in the counterplate 32 which can have a contact surface 38 which is precisely adapted to the spherical bearing surface 36 of the fixed bearing 28. Instead of the contact surface 38, a rounded annular surface can be provided on the counterplate 32 to provide a substantially linear contact with the spherical bearing surface 36.

The bolt 33 is best constructed as a threaded shaft and bears an externally accessible nut or knurled knob 39 which with a corresponding collar or a spacer sleeve 40 presses against the counterplate 32 such that the latter is held in engagement with the spherical bearing surface 36. Instead of the threaded shaft 33 and the nut 39, a plain shaft or the like can be used, having at its free end a toggle lever, cam lever, spring tension means or the like, which produces an axial locking movement of the spacer sleeve 40.

On the main bearing element 31 there is simultaneously disposed a support 41 for a maxillary model and a mandibular model. For this purpose, a bush 42 having a radial flange 43 is affixed to the free end of the bolt 33 and the main bearing element 31 is guided in an axially displaceable manner on the outer circumference of the bush 42. The main bearing element 31 has a flange 44 extending radially and parallel with the flange 43 on bush 42. The main bearing element 31 is provided with an axial groove 45 into which a pin 46 extends in order to secure the displaceable main bearing element 31 against rotation in relation to the bush 42.

The model support 41 consists of a mounting plate 47 having an elongated hole 48 through which the bush 42 extends. The width of the elongated hole 48 is greater than the diameter of bush 42, yet smaller than the diameter of flanges 43 and 44, which can thus engage the mounting plate 47 on both sides. By means of this elongated hole 48 it is possible to perform the cross table movement of the model. A model is affixed on each mounting plate 47 by means of a three-point mounting. For this purpose the mounting plate 47 of the support 41 has two ears 49 which engage the model, which is not shown. Opposite the two ears 49 there is provided a locking device 50 which has a threaded bolt 52 which is adjustable in a threaded bushing 51 and is provided with a knob 53 at its free end. On the end of bolt 52 opposite the knob 53 there is a rotatable pad 54 which grips the model and, when bolt 52 is turned, urges it against the ears 49. The model can thus be affixed to the support 1 and removed therefrom very simply.

Figure 3:
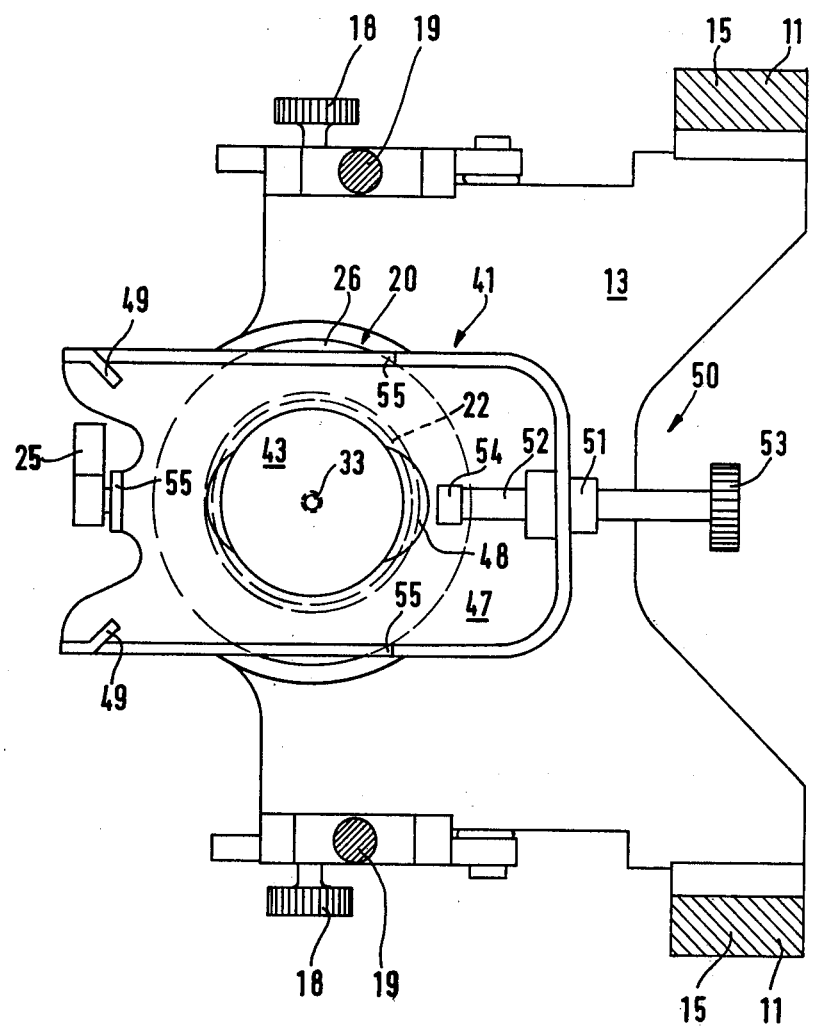
FIG. 3 is a cross sectional view taken along line III—III in FIG. 1.

The cast model of the jaw is thus mounted at the three points 49 and 54 of the support 41. Furthermore, the cast lies upon three points, which are marked 55 in FIG. 3. The lateral points are formed by metal edges having a slight incline of, say, one degree, in order to accommodate casts of different size.

The spherical bearing 30 (FIG. 1) permits the corresponding model support to be tilted between 0° and 15°. Furthermore, a rotation of the absolutely tightly anchored casts and their cross-table displacement can be performed for the purpose of the precise coordination of same with the articulation of the articulator and with one another in harmony with the natural movements. Since, however, not only the universal tilt, rotation and cross-table movements but also the vertical distance between the articulation and the plane of the occlusion which is to be reconstructed or restored in achievable and important, the sliding sleeve 22 can be displaced vertically with the spherical bearing 30 and the support 41. Thus, all movements and orientations in space are possible, the amount of each individual movement being so controlled that not only can a variety of natural differences be compensated but also the common external differences in the shape of hand-made casts.

Two methods of fixation are possible. The cross-table, rotatory and universal tilting movement can be fixed by the nut 39 (FIG. 1). By the rotation of nut 39, the bushing 42 and the counterplate 32 can be locked in relation to one another in the desired position of the bolt 33 by pressing the mounting plate 47 against the main bearing element 31, the latter against the fixed bearing 28, and the latter in turn against the counterplate 32. The central bore 29 is made sufficiently large to permit the movement of bolt 33 within the desired angular range.

The second method of fixation is provided by the screw 24 with the handle 25 and the key 23. This establishes the distance between the mountings 20 for the maxillary model and the mandibular model.

The preparation of the articulator, up to the mechanically determined imitation of the natural mandibular articulation, and its operation, and the procedures for the adjustment of the two models in relation to one another in the many different planes are considerably simplified and expanded. The mountings with the models are quickly exchangeable, if, for example, another work operation is to be performed in the same articulator with other mountings before the work previously begun is complated. Another advantage consists in the arrangement of the three points 49, 54 and 55 for the plaster cast, inasmuch as the invariable ears 49 provide precise reference marks on the surface of the plaster, with permit even a momentary removal of the cast from the support in the mounting 20 and its reinsertion without repositioning. This is useful in the event of interim vacuum formed plates, or in the case of duplication, since such procedures can be performed at any time through the use of the articulator of the invention.

What is claimed is:

1. A dental articulator having a pair of opposed mountings each of which is itself mounted on arms adjustable and fixable in relationship to the opposed mounting and each of which has a spherical axial bearing for adjustably connecting a support for one of the mandibular and maxillary models wherein each of said mountings comprises said spherical axial bearing at least partially contained within a sliding bushing, said sliding bushing axially adjustably and fixably disposed in a bearing ring, said bearing ring disposed in a bore, said bore disposed in a free limb of each of said arms provided by a bent rocker arm, the limbs of which bent rocker arm joined pivotingly about an axis, wherein said sliding bushing of said mounting is engageable by an externally disposed clamping member to secure said sliding bushing with respect to said bearing ring or said bore, respectively, and wherein each of said model supports is connected to a member a portion of which passes through said sliding bushing and said spherical axial bearing for the spherical and axial adjustment and fixation of said model support.

2. A dental articulator according to claim 1 wherein said clamping member comprises a screw threaded within the bearing ring and having a exteriorly disposed handle on one end, said screw abutting at the other end thereof a clamping key disposed in a groove juxtaposed to said sliding bushing.

3. A dental articulator having a pair of opposed mountings each of which is itself mounted on arms adjustable and fixable in relationship to the opposed mounting and each of which has a spherical axial bearing for adjustably connecting a support for one of the mandibular and maxillary models wherein each of said mountings comprises said spherical axial bearing at least partially contained within a sliding bushing, said sliding bushing axially adjustably and fixably disposed in a bearing ring, said bearing ring disposed in a bore, said bore provided within each of said arms, wherein each of said model supports is connected to a member a portion of which passes through said sliding bushing and said spherical axial bearing, for the spherical and axial adjustment and fixation of said model support, and wherein within said sliding bushing there is a wall having an upwardly extending spherical bearing surface of said spherical axial bearing and a central bore extending therethrough, through which central bore passes a bolt of said member, to which bolt said model support is attached, said bolt carrying a counter bearing element, said counter bearing element being fixable for the alignment of said model support with respect to said spherical bearing surface.

4. A dental articulator according to claim 3 wherein said bolt is threaded, it has attached at its free end a main bearing element for said model support and at its opposite end an actuating element of said member.

5. A dental articulator having a pair of opposed mountings each of which is itself mounted on arms adjustable and fixable in relationship to the opposed mounting and each of which has a spherical axial bearing for adjustably connecting a support for one of the mandibular and maxillary models wherein each of said mountings comprises said spherical axial bearing at least partially contained within a sliding bushing, said sliding bushing axially adjustably and fixably disposed in a bearing ring, said bearing ring disposed in a bore, said bore provided within each of said arms, wherein each of said model supports connected to a member a portion of which passes through said sliding bushing and said spherical axial bearing, for the spherical and axial adjustment and fixation of said model, wherein within said sliding bushing there is a wall having an upwardly extending spherical bearing surface of said spherical axial bearing and a central bore extending therethrough, through which central bore passes a threaded bolt of said member to which bolt said model support is attached, said bolt being attached at its free end to a main bearing element for said model support and at its opposite end an actuating element of said member, said bolt carrying a counter bearing element, said counter bearing element being fixable for the alignment of said model support with respect to said spherical bearing surface wherein said main bearing element is disposed axially displaceably, but non-rotatably on a threaded bushing which is fastened to said threaded bolt, said threaded bushing and said main bearing element each having parallel plates between which a mounting plate of said model support is mounted adjustable and fixable by said actuating element of said member.

6. A dental articulator according to claim 5 wherein said mounting plate has an elongated hole whose width is adapted to the outer diameter of said threaded bush.

7. A dental articulator having a pair of opposed mountings each of which is itself mounted on arms adjustable and fixable in relationship to the opposed mounting and each of which has a spherical axial bearing for adjustably connecting a support for one of the mandibular and maxillary models wherein each of said mountings comprises said spherical axial bearing at least partially contained with a sliding bushing, said sliding bushing axially adjustably and fixably disposed in a bearing ring, said bearing ring disposed in a bore, said bore provided within each of said arms, wherein each of said model supports is connected to a member a portion of which passes through said sliding bushing and said spherical axial bearing, for the spherical and axial adjustment and fixation of said model support, wherein within said sliding bushing there is a wall having an upwardly extending spherical bearing surface of said spherical axial bearing and a central bore extending therethrough, through which central bore passes a bolt of said member, to which bolt said model support is attached, said bolt carrying a counter bearing element, said counter bearing element being fixable for the alignment of said model support with respect to spherical bearing surface, and its free end a main bearing element for said model support, and wherein said main bearing element comprises a spherical bearing surface which is in engagement with a recess in said wall of said spherical axial bearing, said recess disposed on the side opposite said spherical bearing surface for said counter bearing element.

8. A dental articulator according to claim 7 wherein said recess has a truncoconical shape.

9. A dental articulator according to claim 7 wherein said recess has a spherical bearing surface disposed concentrically with said spherical bearing surface of said main bearing element and with said surface of said wall opposite said spherical bearing surface of said recess.

10. A dental articulator according to claim 7 wherein each of said mountings including said bearing ring and said sliding bushing, provided with means for urging a clamping member against said sliding bushing, is replaceably mounted within one of said arms, said means including an exteriorly disposed handle.

11. A dental articulator according to claim 10 wherein said bearing ring has centering bores with each of which engage a centering screw carried in each of said arms.

12. A dental articulator according to claim 1 wherein disposed between opposed mountings there is a spacer pin.

* * * * *